(12) United States Patent
Yanai et al.

(10) Patent No.: US 6,743,432 B1
(45) Date of Patent: Jun. 1, 2004

(54) INTERFACE FOR IONTOPHORESIS

(75) Inventors: Shigeo Yanai, Himeji (JP); Katsumi Iga, Suita (JP); Yukihiro Matsumoto, Ikeda (JP); Naruhito Higo, Ryugasaki (JP)

(73) Assignee: Hisamitsu Pharmaceutical Co., Inc., Saga (JP)

(*) Notice: Subject to any disclaimer, the term of this patent is extended or adjusted under 35 U.S.C. 154(b) by 0 days.

(21) Appl. No.: 08/659,370

(22) Filed: Jun. 6, 1996

(30) Foreign Application Priority Data

Jun. 14, 1995 (JP) ............................. 7-172722

(51) Int. Cl.⁷ ................. A61K 9/10; A61K 47/32; A61K 37/00; A61N 1/30
(52) U.S. Cl. .............. 424/400; 424/449; 424/486; 428/305.5; 428/421; 604/20
(58) Field of Search ................ 424/486, 400, 424/449; 428/305.5, 421; 604/20

(56) References Cited

U.S. PATENT DOCUMENTS

| | | | |
|---|---|---|---|
| 4,618,533 A | * | 10/1986 | Steuck |
| 4,845,132 A | * | 7/1989 | Masuoka et al. |
| 4,927,408 A | | 5/1990 | Haak et al. |
| 5,130,024 A | * | 7/1992 | Fujimoto et al. |
| 5,137,633 A | * | 8/1992 | Wang |
| 5,645,527 A | * | 7/1997 | Beck |

FOREIGN PATENT DOCUMENTS

| | | |
|---|---|---|
| EP | 0 411 146 A1 | 2/1990 |
| JP | 6-16535 | 1/1994 |
| JP | 8-98894 | 4/1994 |
| WO | 91/16943 | 11/1991 |
| WO | 92/04938 | 4/1992 |
| WO | 93/01807 | 2/1993 |
| WO | 95/09031 | 4/1995 |

* cited by examiner

Primary Examiner—Edward J. Webman
(74) Attorney, Agent, or Firm—Wenderoth, Lind & Ponack, L.L.P.

(57) ABSTRACT

A hydrophilic membrane having a low adsorptivity for a protein is disposed, as an interface, on a side to be contacted with a skin, and a drug such as a physiologically active peptide is transdermally delivered by iontophoresis. The membrane has an adsorptivity for a protein of not greater than 10 $\mu g/cm^2$. The thickness of the membrane is about 10 to 200 $\mu m$, and the porosity of the membrane is about 60 to 90%. Such membrane includes a hydrophilized fluororesin membrane, a hydrophilized polysulfone membrane and a hydrophilized cellulose derivative membrane.

14 Claims, 5 Drawing Sheets

INTERFACE FOR IONTOPHORESIS

BACKGROUND OF THE INVENTION

1. Field of the Invention

The present invention relates to an interface (skin contactor or patch) which is useful for transdermal or percutaneous drug delivery by means of iontophoresis.

2. Description of the Related Art

Iontophoresis is a system for promoting or accelerating transdermal absorption (endermic absorption) with the use of electricity. The principle of such iontophoresis basically resides in promoting or enhancing transmittance of a drug molecule through a skin barrier due to, in an electric field between an anode and a cathode produced by an electric current, moving force of a positively charged molecule from the anode to the cathode, and a moving force of a negatively charged molecule from the cathode to the anode [see Journal of Controlled Release, 18, 213–220 (1992); Advanced Drug Delivery Review, 9, 119 (1992); and Pharmaceutical Research, 3, 318–326 (1986)].

Recent advances of synthetic technologies and genetic engineering insure pure and mass production of a naturally-occurring peptide or protein, or a peptide or protein in which the amino acid composition of the naturally-occurring peptide or protein is changed, or a chemically-modified derivative thereof. Thus, applications of these peptides or proteins for drugs or medicaments have been expected. On the other hand, a strict control of administration (dosage) of these peptides or proteins, which exhibit various physiological activities in an extremely small amount, is required for exhibition of the maximum drug effect and minimizing a side effect or adverse reaction in a specific disease.

Further, such physiologically active peptide or protein is generally decomposed by a digestive fluid or juice in a gastrointestinal tract (digestive tract) or hydrolyzed by a hydrolase present in the digestive tract wall, and hence absorption efficacy of the peptide or protein can hardly be improved with effectiveness. Therefore, for expecting a sufficient drug effect, the physiologically active peptide or protein is usually administered not orally but via an injection. Administration as an injectable preparation, however, causes great pain to a patient to be administered and burdens him with a heavy load since such injectable preparation can not be administered by himself.

In the field of pharmaceutical preparation, the iontophoresis has been intensively researched as a new drug delivery system. That is, use of the iontophoresis provides an administration of a drug, which has been administered as an injectable preparation, by a patient himself, and hence ensures expanded possibility of applications as therapy at home. Further, control of drug absorption time can be effected by a precise control or regulation of electric current or voltage application time. In particular, when the iontophoresis is applied to a supplemental therapy (treatment) of an endogenous compound in consideration of circadian rhythm of a living body, more effective therapy with it is expected to be realized.

In an administration system using the iontophoresis having such advantages, use is generally made of an electrode for applying an electric current by means of a direct-current electric power unit, a drug-holder (an interface as a skin contact or patch) which is conductible to the electrode and capable of making contact with the skin, and a reference electrode. As an interface, there have been reported an electrically nonconductive interface composed of an organic drug-supporting layer (e.g. a drug-supporting layer comprising a paper material, a woven or nonwoven fabric and other fabric material, a fibrous material, a synthetic resin continuous foam or water-absorbable resin and other sponge or porous body), and an electrically nonconductive interface comprising an inorganic support (e.g. a ceramic porous body, or a ceramic having a porous or capillary structure).

However, when a drug is supported on these drug-support by means of coating or impregnation, or supported in semi-dry or dry conditions, satisfactorily sufficient amount of transdermal drug absorption can not be expected. Accordingly, the bioavailability of the drug can hardly be improved. The reason of such low amount of transdermal absorption of the drug may be considered that the drug such as a physiologically active peptide or protein is adsorbed to the drug-support with a decreased bioavailability of the drug.

Japanese Patent Application Laid-open No. 16535/1994 (JP-A-6-16535) proposes the use of an interface (skin contactor) for iontophoresis as produced by coating a porous or capillary structure composed of an electrically nonconductive material with a high molecular weight protein such as a bovine serum albumin, a human serum albumin or gelatin for inhibiting the adsorption of a drug and hence ensuring effective improvement of transdermal absorptivity with a small amount of the drug. This literature describes that a nylon porous body (e.g. Biodyne) is preferable as a porous or capillary structure.

In the above interface, however, effective dose of the drug is remarkably decreased with elapse of time and hence effective absorption of the drug can hardly be expected. It is probably because of the adsorption of the drug to the structure as a base material of the interface and poor drug releasability by means of the iontophoresis. Therefore, effective and precise transdermal drug administration with high reproducibility and high bioavailability can,hardly be expected. That is, in the above interface, it is difficult to hold or support a physiologically active peptide or protein with a high retention and to administer them transdermally with a high bioavailability.

SUMMARY OF THE INVENTION

It is, therefore, an object of the present invention to provide an interface (skin contact) for iontophoresis which ensures effective and precise transdermal drug delivery with high bioavailability and high reproducibility.

It is another object of the invention to provide an interface for iontophoresis which inhibits the decrease of a retention amount of an effective drug and provides high releasability and effective transdermal delivery of the drug.

A further object of the invention is to provide an interface for iontophoresis which ensures improved or enhanced releasability and bioavailability of a physiologically active peptide or protein.

It is a yet another object of the invention to provide a method for promoting transdermal absorption of a drug with the use of the interface.

The inventors of the present invention made intensive investigations to accomplish the above-mentioned objects, and found that an arrangement of a membrane having a hydrophilic property and a low adsorptivity for a peptide or protein in a side or surface to be made contact with a skin ensures rapid release of a drug after contact with a dissolution liquid when it is a physiologically active peptide or protein and provides transdermal drug delivery with an extremely high bioavailability and excellent reproducibility. The invention has been accomplished on the basis of the above findings and further investigations.

Thus, (1) the interface for iontophoresis of the invention is provided with a membrane having a low adsorptivity for a protein including peptide (hereinafter referred to briefly as protein). In the interface for iontophoresis, (2) the adsorptivity for a protein of the membrane may be 0 to about 10 μg per 1 cm², (3) the thickness of the membrane may be about 10 to 200 μm, and (4) the porosity of the membrane may be about 60 to 90%. (5) The membrane includes membranes of hydrophilized fluororesins, hydrophilized cellulose derivatives, hydrophilized polysulfones and others.

It should be understood that, in the present specification, the term "low adsorptivity for a protein" means, for example, that adsorptivity for a peptide fragment of the N-terminus (1→34-position) of a human PTH (hereinafter briefly referred to as "hPTH (1→34)") is not greater than 10 μg/cm².

DETAILED DESCRIPTION OF THE INVENTION

Figure 1:
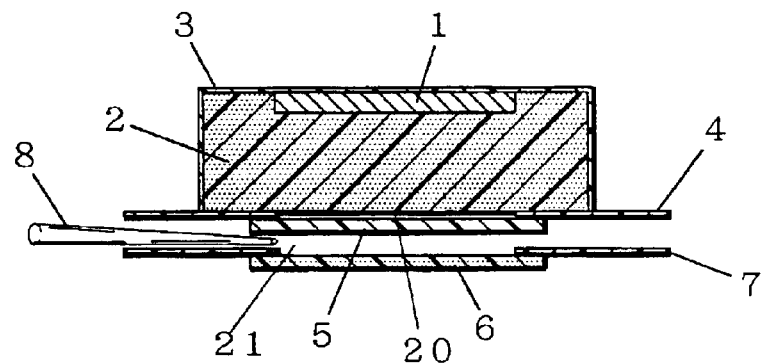
FIG. 1 is a cross sectional view illustrating an embodiment of an applicator.

The present invention is now described in detail with referring to the drawings where necessary.

As a material for the hydrophilic membrane having a low adsorptivity for a protein (hereinafter may simply be referred to as "the hydrophilic membrane" or "the membrane") constituting the interface for iontophoresis, use may be made of hydrophilic materials which ensure retention of a drug in dry conditions, provide permeation of the drug and have a low adsorptivity for a protein. The hydrophilic membrane made from such hydrophilic material includes membranes each having a high wettability with respect to water, such as hydrophilized hydrophobic (or water-repellent) polymer membranes and hydrophobic polymer membranes each containing a hydrophilic substance.

As the hydrophilized hydrophobic polymer membrane, there may be mentioned, for example, membranes formed with a hydrophilized fluororesin (e.g. a membrane of a homo- or co-polymer which comprises, as a constitutive component, a fluorine-containing monomer introduced with a hydrophilic group such as "Hydrophilic Durapore" manufactured by Millipore Co., Ltd., and a surface-modified membrane, in which the surface of a homo- or co-polymer comprising a fluorine-containing monomer as constitutive component is modified to be hydrophilic, such as "Hydrophilized Polytetrafluoroethylene", Toyo Roshi Co., Ltd.), membranes formed with a hydrophilized polysulfone (e.g. "SUPOR", Gelman Science Co., Ltd.), membranes made from a hydrophilized cellulose derivatives (e.g. hydrophilized cellulose mono-acetate or hydrophilized cellulose tri-acetate) or the like (e.g. various filter papers and ion exchange filter papers manufactured by Toyo Roshi Co., Ltd.) and so on. The fluorine-containing monomer introduced with a hydrophilic group includes, for instance, a fluoroethylene (1-fluoroethylene) introduced with a hydrophilic group, a vinylidene fluoride (i.e. vinylidene fluoride as 1,1-difluoroethylene) and 1,2-difluoroethylene, each of which is introduced with a hydrophilic group. As examples of the polymer formed with such monomer, there may be mentioned a hydrophilized polyfluoroethylene, a hydrophilized fluoroethylene-tetrafluoroethylene copolymer, a hydrophilized fluoro-ethylene-hexafluoropropylene copolymer, a hydrophilized ethylene-fluoroethylene copolymer, a hydrophilized ethylene-chlorotrifluoroethylene copolymer, a hydrophilized poly (vinylidene fluoride), a hydrophilized fluoroethylene-vinylidene fluoride copolymer, a hydrophilized ethylene-vinylidene fluoride copolymer and so forth. The species of the hydrophilic group introduced into the fluorine-containing monomer is not strictly limited, and includes, for example, a hydroxyl group, a carboxyl group, an amino group, an N-substituted amino group (e.g. a mono- or di-$C_{1-4}$ alkylamino group), a (poly)oxyalkylene group and other ether groups, a hydrophilic alkyl group (e.g. hydroxymethyl, hydroxyethyl, hydroxypropyl and other hydroxy-$C_{1-4}$ alkyl groups, a carboxymethyl group, a carboxyethyl group and other carboxy-$C_{1-4}$ alkyl groups, aminomethyl, aminoethyl and other amino-$C_{1-4}$ alkyl groups. methylaminomethyl, dimethylaminomethyl, dimethylaminoethyl and other mono- or di-$C_{1-4}$ alkylamino-$C_{1-4}$ alkyl groups, etc.). These hydrophilic groups may practically be bonded to a carbon atom as a substitute for a hydrogen atom.

The hydrophilized fluororesin may practically comprise a repeating unit shown by the following formula.

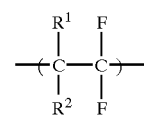

wherein $R^1$ and $R^2$ respectively represent a hydrophilic alkyl group.

As the hydrophilic alkyl group, there may be mentioned, for instance, a hydroxyalkyl group (in particular, a hydroxy-$C_{2-3}$ alkyl group) and a (poly)oxyalkylene group (especially, a (poly)oxy-$C_{2-4}$ alkylene group). The hydroxyalkyl group may be derived from a polymerizable compound having a hydroxyl group [e.g. hydroxyethyl (meth)acrylate, hydroxypropyl (meth)acrylate or 4-hydroxybutyl (meth)acrylate]. The (poly)-oxyalkylene group may be derived from a polymerizable compound having an ether group, such as a (poly)oxyalkylene glycol mono(meth)acrylate [e.g. diethylene glycol mono(meth)acrylate, triethylene glycol mono (meth)acrylate, tetraethylene glycol mono(meth)acrylate, polyethylene glycol mono(meth)acrylate, dipropylene glycol-mono(meth)acrylate, tripropylene glycol mono (meth)acrylate, tetrapropylene glycol mono(meth)acrylate, polypropylene glycol mono(meth)acrylate, etc.], a (poly) oxyalkylene glycol di(meth)acrylate [e.g. ethylene glycol di(meth)acrylate, diethylene glycol di(meth)acrylate, triethylene glycol di(meth)acrylate, tetraethylene glycol di(meth) acrylate, polyethylene glycol di(meth)acrylate, propylene glycol di(meth)acrylate, dipropylene glycol di(meth) acrylate, tripropylene glycol di(meth)acrylate, tetrapropylene glycol di(meth)acrylate, polypropylene glycol di(meth) acrylate, tetramethylene glycol di(meth)acrylate and so forth].

Such hydrophilic alkyl group may be introduced by means of graft polymerization of the polymerizable compound to the surface, including pores, of a porous fluororesin membrane, or introduced by coating with the polymer derived from the polymerizable compound.

The hydrophilized hydrophobic membrane is prepared by treating hydrophobic polymer membrane with a hydrophilic substance physically. Examples of such hydrophilized hydrophobic membranes include various membranes prepared from hydrophobic polymer membrane incorporated with a suitable wetting agent (e.g. polyvinylpyrrolidone, glycerin), such as a hydrophilized cellulose acetate membrane (e.g. "Asymmetric Ultrafilter" manufactured by Sartorius Co., Ltd.; "Cellulose Acetate Type Membrane" manufactured by Toyo Roshi Co., Ltd.), a hydrophilized polycarbonate membrane (e.g. "Isopore Membrane" manufactured by Millipore Co., Ltd.), a hydrophilized polytetrafluoroethylene membrane (e.g. "Omnipore Membrane" manufactured by Millipore Co., Ltd.) and a hydrophilized polysulfone membrane (e.g. "Tuffryn" manufactured by Gelman Science Co., Ltd.), and a hydrophilized non-woven membrane such as a polyester non-woven treated with cellulose acetate and wetting agents (e.g. "Coated Type Membrane" manufactured by Toyo Roshi Co., Ltd.).

These hydrophilic membranes have an extremely low adsorptivity for a physiologically active peptide or protein and provides a high permeability of a drug-containing solution or a dissolution liquid for dissolving the drug and high dissolution rate of the drug. The preferred membrane includes a membrane having a low adsorptivity for a protein and a high retentivity for the drug, such as a hydrophilized fluororesin membrane and a hydrophilized cellulose derivative membrane. Such cellulose derivative is exemplified by celulose acetate, methylcellulose, ethylcellulose, hydroxypropylcellulose, hydroxypropylmethylcellulose phthalate, etc. Among them, a hydrophilized poly (vinylidene fluoride) (e.g. "Hydrophilic Durapore" manufactured by Millipore Co., Ltd.) and a hydrophilized cellulose acetate membrane (e.g. "Cellulose Acetate Type Membrane" manufactured by Toyo Roshi Co., Ltd.), and a hydrophilized polyester non-woven coated with cellulose acetate and wetting agents (e.g. "Coated Type Membrane" manufactured by Toyo Roshi Co., Ltd.) can advantageously be employed.

The hydrophilic membrane (thin film) is characterized by low adsorptivity for a protein and hence a small adsorption amount of such protein. The adsorptivity of the protein with respect to the membrane is, for example, not greater than 10 $\mu g/cm^2$ (0 to about 10 $\mu g/cm^2$, preferably not greater than 8 $\mu g/cm^2$ (e.g. 0 to about 6 $\mu g/cm^2$), and more preferably not greater than 6 $\mu g/cm^2$ (e.g. 0 to about 4 $\mu g/cm^2$). The adsorptivity for the protein can be determined by a conventional technology, such as a process which comprises dipping the membrane into 300 $\mu l$ of a distilled water containing 40 $\mu g$ of hPTH (1→34) and a tracer amount of $^{125}$I-labelled hPTH (1→34) at room temperature for 2 hours, removing off the solution by suction, washing the membrane three times with 1 ml of a distilled water and determining a residual radioactivity.

The hydrophilic membrane has a porous structure. The pore size of the membrane can be selected within a range not interfering with retention amount (holding amount) and/or releasability of the drug and ensuring rapid release of the drug after the contact with a dissolution liquid, and providing formation of a highly concentrated drug dissolution layer on a surface or side to be made contact with a skin, and the mean pore size is about 0.01 to 20 $\mu m$, preferably about 0.1 to 15 $\mu m$ (e.g. about 0.1 to 10 $\mu m$) and more preferably about 1 to 10 $\mu m$ (e.g. about 2 to 8 $\mu m$), for example. The porosity (percentage of void) of the membrane may be, for instance, about 60 to 90%, preferably about 65 to 90% and more preferably about 65 to 85%. The pore of the membrane may be formed by a conventional technologies such as extending process which comprises extending the film in a film-forming step, fluid-extending, phase-separation, elution or irradiation of a high energy radiation.

The thickness of the hydrophilic membrane may be selected within a range according to the holding amount (retention amount) of the drug, and is, for example, about 0.1 to 500 $\mu m$, preferably about 1 to 300 $\mu m$ and more preferably about 10 to 200 $\mu m$. The hydrophilic membrane may practically have a thickness of about 20 to 150 $\mu m$. The area of the membrane may liberally be selected according to the retention amount of the drug, and is, for instance, about 1 to 100 $cm^2$, and preferably about 2 to 50 $cm^2$.

The membrane may be non-deformable, but it may preferably have flexibility or softness.

The hydrophilic membrane may be treated with an ionic surfactant for the purpose of further inhibiting adsorption of a protein. The ionic surfactant (surface active agent) includes anionic surfactants, cationic surfactants and amphoteric surfactants. As examples of the anionic surfactant, there may be mentioned metallic soaps of fatty acids, alkyl sulfates (e.g. a sodium salt), alkylbenzenesulfonates (e.g. a sodium salt), alkylnaphthalenesulfonates, α-olefin sulfonates (for instance a sodium salt), N-acylamino acid salts (e.g. a sodium salt) and dialkyl-2-sulfosuccinates (for example a sodium salt). These anionic surfactants may be used singly or in combination.

The cationic surfactant includes, for instance, N-ethylalkaneamideammonium halides (e.g. N-ethyl-$C_{8-20}$ alkaneamideammonium chloride), alkylpyridinium halides (e.g. an N-$C_{10-20}$ alkylpyridinium bromide), quaternary ammonium salts and so forth. Examples of the quaternary ammonium salt include alkyltrimethylammonium halides (e.g. a $C_{8-20}$ alkyl-trimethylammonium chloride), di-alkyldimethylammonium halides (e.g. a di-$C_{8-20}$ alkyl-dimethylammonium chloride), alkylbenzyl-dimethylammonium halides shown by the following formula

$[C_6H_5CH_2N(CH_3)_2R]^+X^-$ wherein R represents an alkyl group and X represents a halogen atom, [e.g. a $C_{8-20}$ alkylbenzyldimethylammonium chloride (benzalkonium chloride), a 4-$C_{1-10}$ alkyl-phenyloxyethoxyethylbenzyldimethylammonium chloride (e.g. benzethonium chloride)] and so forth. Such cationic surfactants can also be employed independently or in combination.

Examples of the amphoteric surfactant include an alkyl betaine, an alkyl diethylenetriaminoacetate and the like.

Preferable ionic surfactant includes cationic surfactants, in particular quaternary ammonium salts. The alkylbenzyldimethylammonium halides shown by the above formula (e.g. benzalkonium chloride, benzethonium chloride) can advantageously be employed among others.

The treating amount of the ionic surfactant relative to the hydrophilic membrane is for example about 0.10 to 50 $\mu g$, preferably about 0.10 to 30 μg and more preferably about 0.12 to 12 μg of the ionic surfactant relative to 1 cm² of the membrane.

The treating amount of the ionic surfactant may be about 0.001 to 10% by weight, preferably about 0.005 to 5% by weight and more preferably about 0.01 to 1% by weight relative to the hydrophilic membrane. The hydrophilic membrane may practically be treated with about 0.005 to 1% by weight, relative to the membrane, of the ionic surfactant.

The use of the membrane as disposed on a side or surface, with which a skin is to contact, provides a contact of the drug with a skin through the membrane in a definite area, and hence ensures effective transdermal absorption of the drug with excellent reproducibility.

The drug to be administered through the membrane (interface) is not particularly limited as far as being transdermally or percutaneously absorbable and being water-soluble, and various physiologically active peptides or proteins or nucleic acid, or non-peptide physiologically active compounds of a low molecular weight can be employed. The molecular weight of the physiologically active peptide or protein or nucleic acid is, for instance, about 100 to 30,000 (preferably about 200 to 20,000, more preferably about 500 to 10,000 and practically about 500 to 8,000). The molecular weight of the non-peptide physiologically active compound with a low molecular weight is not greater than about 1,000 (e.g. about 100 to 1,000).

As the nonpeptide physiologically active compound with a low molecular weight, use may be made of various low molecular weight compounds including central nervous system drugs, antiallergic agents, circulatory drugs, vasoconstrictors, analgesic agents, respiratory drugs, drugs for digestive system, hormone agents, metabolic drugs, antitumor drugs, antibiotics, chemotherapeutic drugs and so on. The preferred drug includes a physiologically active peptide or protein. The molecular weight of the physiologically active peptide or protein may practically be about 100 to 30,000 and preferably about not more than 8,000.

As the physiologically active peptide, there may be mentioned, for example, the following peptides:

Luteinizing hormone-releasing hormone (LH-RH), derivatives each having a similar function or activity to LH-RH, such as nafarelin and a polypeptide shown by the following formula (I):

(Pyr) Glu-R¹-Trp-Ser-R²-R³-R⁴-Arg-Pro-R⁵    (I)

wherein $R^1$ represents His, Tyr, Trp or p-NH$_2$-Phe, $R^2$ represents Tyr or Phe, $R^3$ indicates Gly or a D-amino acid residue, $R^4$ denotes Leu, Ile or Nle, $R^5$ represents Gly-NH-$R^6$, where $R^6$ denotes a hydrogen atom or a lower alkyl group which may have a hydroxyl group, or NH-$R^6$, where $R^6$ has the same meaning as above, or a salt thereof [see U.S. Pat. No. 3,853,837, U.S. Pat. No. 4,008,209, U.S. Pat. No. 3,972,859, British Patent No. 1423083, Proceedings of the National Academy of Science, 78, 6509–6512 (1981)].

As examples of the D-amino acid residue shown by $R^3$ in the formula (I), there may be mentioned α-D-amino acids each having 9 carbon atoms or less (e.g. D-Leu, Ile, Nle, Val, Nval, Abu, Phe, Phg, Ser, Thr, Met, Ala, Trp, α-Aibu). These amino acids may have a protective group (e.g. t-butyl, t-butoxy or t-butoxycarbonyl group). The lower alkyl group shown by $R^6$ includes, for example, alkyl groups each having about 1 to 6 carbon atoms (e.g. methyl, ethyl, propyl, isopropyl, butyl and t-butyl groups).

Incidentally, a salt (e.g. a salt with an acid) or a metallic complex compound of the peptide shown by the formula (I) can also be used in the similar manner as the peptide of the formula (I).

Among the polypeptides shown by the formula (I), a polypeptide (TAP-144) wherein $R^1$=His, $R^2$=Tyr, $R^3$=D-Leu, $R^4$=Leu and $R^5$=NHCH$_2$—CH$_3$ is preferably employed.

LH-RH antagonists such as a polypeptide shown by the following formula (II):

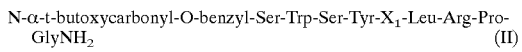

N-α-t-butoxycarbonyl-O-benzyl-Ser-Trp-Ser-Tyr-X$_1$-Leu-Arg-Pro-GlyNH$_2$    (II)

wherein $X_1$ represents D-Ser or D-Trp, or a salt thereof [see U.S. Pat. Nos. 4,086,219, 4,124,577, 4,253,997 and 4,317, 815].

Snake poison (venom) peptides each having antagonistic activity against GPIIb/IIIa, such as barbourin, peptides having Arg-Gly-Asp sequence, such as Arg-Gly-Asp-Ser, Gly-Arg-Gly-Asp-Ser-Pro, SK&F-106760 (cyclo-S,S-[Ac-Cys (N$^\alpha$-methyl)Arg-Gly-D-Asn-penicillamine]-NH$_2$), and other peptide-like compounds having a similar function or activity, such as (S)-4-[(4-amidinobenzoyl)glycyl]-3-methoxy-carbonylmethyl-2-oxopiperazine-1-acetic acid, (S)-4-(4-guanidinobenzoylamino)acetyl-3-[3-(4-guanidinobenzoylamino)]propyl-2-oxopiperazine-1-acetic acid hydrochloride, MK-383 (2-S-(n-butylsulfonylamino)-3-[4-(N-piperidin-4-yl)butyloxyphenyl)]-propionic acid-HCl), L-700462 (L-Tyr-N-(butylsulfonyl)-O-[4-(piperidinyl) butyl]mono-hydrochloride), SC-56484 (ethyl [[4-(aminoiminomethyl) phenyl]amino]-1,4-dioxybutyl]amino-4-pentinoate), Ro-44-9883 ([1-[N-(p-amidinophenyl)-L-Tyr]-4-piperidinyl]acetic acid), DMP728 (cyclic [D-2-aminobutylyl-N-2-methyl-L-Arg-Gly-L-Asp-3-aminomethyl-benzoic acid] methanesulfonate.

Insulin; somatostatin, somatostatin derivatives, such as a polypeptide shown by the following formula (III):

(III)

H—L-Ala-Y-L-Cys-L-Lys-Z-L-Phe-L-Phe-D-Trp-L-Lys-L-

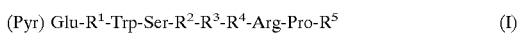

Thr-L-Phe-L-Thr-L-Ser-L-Cys—OH wherein Y represents D-Ala, D-Ser or D-Val, Z represents Asn or Ala, or a salt thereof [see U.S. Pat. Nos. 4,087,390, 4,093,574, 4,100,117 and 4,253,998], growth hormone, growth hormone-releasing hormone (GRH); prolactin; adrenocorticotropic hormone (ACTH); melanocyte-stimulating hormone (MSH); thyroid stimulating hormone-releasing hormone (TRH), and derivatives thereof, such as a compound shown by the following formula (IV):

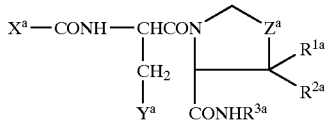

(IV)

$X^a$—CONH—CHCON, $Z^a$, $R^{1a}$, $R^{2a}$, $Y^a$, CONHR$^{3a}$, CH$_2$ wherein $X^a$ represents a 4- to 6-membered heterocyclic group, $Y^a$ denotes imidazol-4-yl or 4-hydroxylphenyl group, $Z^a$ represents CH$_2$ or S, $R^{1a}$ and $R^{2a}$ independently represent a hydrogen atom or a lower alkyl group, and $R^{3a}$ represents a hydrogen atom or an optionally substituted aralkyl group, or a salt thereof [see Japanese Patent Application Laid-open No. 121273/1975 (JP-A-50-121273), Japanese Patent Application Laid-open No. 116465/1977 (JP-A-52-116465)].

Thyroid stimulating hormone (TSH); luteinizing hormone (LH): follicle-stimulating hormone (FSH); parathyroid hormone (PTH), derivatives each having a similar function or activity to the parathyroid hormone, such as a peptide shown by the following formula (V)

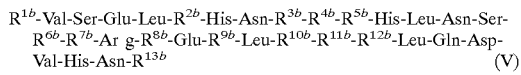

wherein $R^{1b}$ represents Ser or Aib, $R^{2b}$ represents Met or a naturally-occurring fat-soluble amino acid, $R^{3b}$ denotes Leu, Ser, Lys or an aromatic amino acid, $R^{4b}$ represents Gly or a D-amino acid, Rs b denotes Lys or Leu, $R^{6b}$ represents Met or a naturally-occurring fat-soluble amino acid, $R^{7b}$ denotes Glu or a basic amino acid, $R^{8b}$ represents Val or a basic amino acid, $R^{9b}$ represents Trp or 2-(1,3-dithiolan-2-yl)Trp, $R^{10b}$ denotes Arg or His, $R^{11b}$ represents Lys or His, $R^{12b}$ denotes Lys, Gln or Leu, and $R^{13b}$ represents Phe or Phe-$NH_2$, or a salt thereof [see Japanese Patent Application Laid-open No. 32696/1993 (JP-A-5-32696), Japanese Patent Application Laid-open No. 247034/1992 (JP-A-4-247034), EP-A-510662, EP-A-477885, EP-A-539491], hPTH (1→34) [G. W. Tregear et al., Endocrinology, 93, 1349–1353 (1973)]; vasopressin, vasopressin derivatives {desmopressin [see Journal of Society of Endocrinology, Japan, 54, No. 5, 676–691 (1978)]}.

Oxytocin; calcitonin, derivatives each having a similar function to calcitonin, such as a compound shown by the following formula (VI):

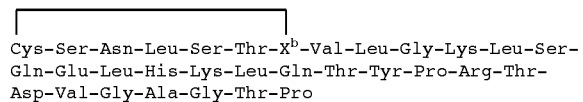

(VI)

wherein $X^b$ represents 2-aminosberic acid, or a salt thereof [Endocrinology, 1992, 131/6 (2885–2890)]. glucagon; gastrins; secretin; pancreozymin; cholecysto-kinin; angiotensin; human placental lactogen; human chorionic gonadotropin (HCG).

Enkephalin, enkephalin derivatives, such as a peptide shown by the following formula (VII):

(VII)

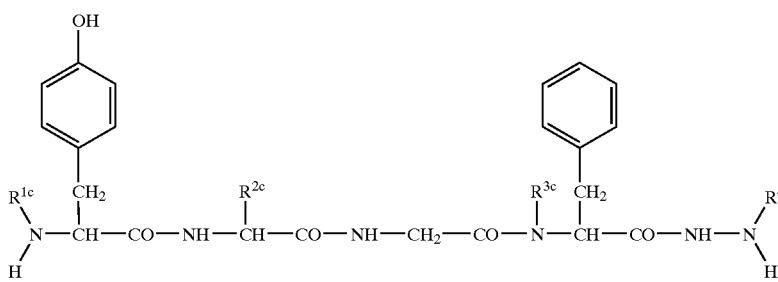

wherein $R^{1c}$ and $R^{3c}$ respectively represent a hydrogen atom or an alkyl group having 1 to 6 carbon atoms, $R^{2c}$ represents a hydrogen atom or a residue of a D-α-amino acid, $R^{4c}$ denotes a hydrogen atom or an optionally substituted aliphatic acyl group having 1 to 8 carbon atoms, or a salt thereof (see U.S. Pat. No. 4,277,394 and EP-A-31567) and other oligopeptides and endorphins.

Kyotorphine; interferons (α-, β-, γ-interferons); interleukins (e.g. interleukins I to XI); tuftsin; thymopoietin; thymostimulin; thymus humoral factor THF); factor of thymus in serum (FTS) and their derivatives, such as a peptide shown by the following formula (VIII):

(VIII)

wherein $X^d$ represents L- or D-Ala, $Y^d$ and $Z^d$ independently represent Gly or a D-amino acid residue having 3 to 9 carbon atoms, or a salt thereof (see U.S. Pat. No. 4,229,438); and other thymus hormones [e.g. thymocin $α_1$ and $β_4$, thymic factor X, etc. "Journal of Clinical Experimental Medicine (IGAKU NO AYUMI)" 125, No. 10, 835–843 (1983)].

Tumor necrosis factor (TNF): colony stimulating factor (CSF); motilin; dynorphin; bombesin; neurotensin; cerulein; bradykinin; urokinase; asparaginase; kallikrein; substance P; nerve growth factor; factor VII and factor IX of blood coagulation factors; lysozyme chloride; polymyxin B; colistin; gramicidin; bacitracin; protein synthesis-stimulating peptide (British Patent No. 8232082); gastric inhibitory polypeptide (GIP); vasoactive intestinal polypeptide (VIP); platelet-derived growth factor (PDGF); growth hormone-releasing factor (GRF, somatoclinine); born morphogenetic protein (BMP); epithelium growth factor (EGF); preprocortistatin (Nature, 381, 242–245, 1996), erythropoietin and so on.

These physiologically active peptides may be human peptides, or peptides derived from other animals such as bovines, swine, chickens, salmon, eel and so forth. Further, the peptide may be a chimera of a human peptide and a peptide derived from the above animal, or an active derivative in which a part of the structure of the peptide has been changed. By way of an example, the insulin may be an insulin derived from a swine. As to the calcitonin, use may be made of a calcitonin derived from a swine, a chicken, salmon, or eel, or a peptide which is a chimera of a human and salmon and is shown by the following formula (IX) [Endocrinology, 1992, 131/6 (2885–2890)]:

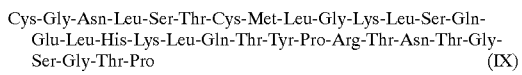

Preferred examples of the drug include physiologically active peptides and their derivatives, such as a calcitonin, adrenocorticotropic hormone, parathyroid hormone (PTH), hPTH (1→34), insulins, secretin, oxytocin, angiotensin, β-endorphin, glucagon, vasopressin, somatostatin, gastrins, luteinizing hormone-releasing hormone, enkephalins, neurotensin, atrial natriuretic peptide, growth hormone, growth hormone-releasing hormone, bradykinin, substance P, dynorphin, thyroid stimulating hormone, prolactin, interferons, interleukins, G-CSF, glutathione peroxidase, superoxide dismutase, desmopressin, somatomedin, endothelin, and their salts. Further, nucleic acids, oligonucleotides and various antigenic proteins may also be employed.

The salt of the physiologically active peptide or its derivative includes, for instance, a salt with an inorganic acid such as hydrochloric acid, sulfuric acid, hydrobromic acid and phosphoric acid; a salt with an organic acid such as formic acid, acetic acid, propionic acid, glycolic acid, oxalic acid, succinic acid, tartaric acid, citric acid, benzenesulfonic acid and p-toluenesulfonic acid; a complex salt with an inorganic compound such as calcium and magnesium.

The nonpeptide physiologically active compound includes compounds each having a molecular weight of about 1,000 or less and having pharmacological activity. The species of the nonpeptide physiologically active compound is not particularly limited, and as the compound, there may be mentioned for example antibiotics, antimycosis (antifungal drugs), hypolipidermic drugs, circulatory drugs, vasoconstrictors, antiplatelet drugs, antitumor drugs, antipyretic, analgesic and/or anti-inflammatory agents, antitussive-expectorant agents, sedatives, muscle relaxants, antiepileptic drugs, antiulcer drugs, antidepressant agents, antiallergic agents, cardiotonics, antiarrhythmic agents, vaso-dilators, hypotensive-diuretic agents, drugs for diabetes, anticoagulants, hemostatic agents, antituberculosis drugs, hormones, narcotic antagonists, bone resorption-inhibitory agents, osteogenetic promoting agents, angiogenesis inhibitors and so forth.

The antibiotic includes, for instance, gentamycin, lividomycin, sisomycin, tetracycline hydrochloride, ampicillin, cefalothin, cefotiam, cefazolin, tienamycin, sulfazecin and so on.

The antifungal agent includes, for example, 2-[(1R,2R)-2-(2,4-difluorophenyl-2-hydroxy-1-methyl-3-(1H-1,2,4-triazol-1-yl)propyl]-4-[4-(2,2,3,3-tetrafluoropropoxy) phenyl]-3(2H,4H)-1,2,4-triazolone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone and the like.

Examples of the hypolpidermic drug (antihyperlipidermic drug) include paravastatin and simvastatin. The circulatory drug includes delapril hydrochloride, for instance.

Examples of the vasoconstrictors include prostaglandin $E_2$ and prostaglandin F.

As the antiplatelet drug, there may be mentioned, for exmaple, ticlopidine, cilostazol, limaprostat, aspirin and the like.

The antitumor drug (antineoplastic agent) includes, for instance, bleomycin hydrochloride, actinomycin-D, mitomycin-C, adriamycin and fluorouracil.

As examples of the antipyretic, analgesic and/or antiinflammatory agent, there may be mentioned sodium salicylate, sulpyrine, indomethacin sodium, hydromorphone, morphine hydrochloride, fentanyl, buprenorphine and so forth.

The antitussive/expectorant agent includes, for example, ephedrine hydrochloride, codeine phosphate and picoperidamine hydrochloride.

As the sedative, there may be mentioned chlorpromazine hydrochloride, and atropine sulfate, for instance. Examples of the muscle relaxant are pridinol methanesulfonate, tubocurarine chloride and so on.

As the antiepileptic agent, there may be mentioned for instance phenytoin sodium, ethosuximide and so forth. The antiulcer drug includes, for example, metoclopramide. As the antidepressant, there may be mentioned for instance imipramine and phenelzine sulfate.

Examples of the antiallergic drug are diphenhydramine hydrochloride, tripelennamine hydrochloride, clemizole hydrochloride and the like.

As the cardiotonic, there may be mentioned trans-n-oxocamphor and theophyllol, for example. The antiarrhythmic agent includes, for instance, propranolol hydrochloride and oxprenolol hydrochloride. Examples of the vasodilator include oxyfedrine hydrochloride, tolazoline hydrochloride, bamethan sulfate and so forth. The hypotensive-diuretic agent includes, for instance, pentolinium, hexamethonium bromide and so on.

Examples of the antidiabetic agent (hypoglycemic drug) include glymidine sodium, glipizide, metformin, pioglitazone, Trolitazone and the like. As the anti-coagulant, use may be made of sodium citrate, for example.

The hemostatic includes menadione sodium bisulfite, acetomenaphtone and tranexamic acid, typically speaking. As the antituberculosis drug, there may be mentioned, for example, isoniazid and ethambutol.

Examples of the hormone drug include β-estradiol, testosterone, prednisolone succinate, dexamethasone sodium sulfate, methimazole and so forth. The narcotic antagonist includes, for example, levalorphan tartrate and nalorphine hydrochloride. As example of the bone resorption inhibitory drug, there may be mentioned (sulfur-containing alkyl)aminomethylene bisphophoate.

Examples of the osteogenetic promoting agents include (2R,4S)-(−)-N-[4-(diethoxyphosphorylmethyl)-phenyl]-1,2,4,5-tetrahydro-4-methyl-7,8-methylenedioxy-5-oxo-3-benzothiepine-2-carboxamide.

As the angiogenesis inhibitor, there may be mentioned, for instance, a vascularization inhibitory steroid [see Science 221, 719 (1983)], fumagillol derivatives, [e.g. O-monochloroacetylcarbamoylfumagillol, O-dichloroacetylcarbamoylfumagillol (see EP-A-357061, EP-A-359036, EP-A-386667 and EP-A-4152943)].

When the drug is transdermally administered or delivered with the use of iontophoresis, the drug may previously be held by the drug holder, or a solution of the drug may be injected to the neighborhood of the membrane when used. When the drug is held by the drug holder, it may be held or supported in dry conditions throughout the whole of the membrane, but it may preferably be held at least in an area to be contacted with a skin of a living body. The holding or supporting of the drug to the interface (skin contactor) can be effected by, for example, dropwise-addition, injection, impregnation, application (coating), spraying and so on. The drug held or supported by the interface in dry conditions can easily be dissolved by supplying or applying a dissolution liquid to the drug, typically speaking.

The proportion of the drug to be applied to the hydrophilic membrane (skin contactor) may only be an effective amount according to the species of the drug, the species of the animal to be administered, the site or part to be administered and other factors. The relative amount of the drug to 1 $cm^2$ of the membrane is, for instance, about 0.1 to 100 μg, preferably about 0.5 to 70 μg and more preferably about 1 to 50 μg.

Incidentally, the drug may be held or supported by the hydrophilic membrane together with the ionic surfactant (in particular, an alkylbenzyldimethylammonium halide and other cationic surfactants). The holding or supporting amount of the ionic surfactant can liberally be selected within a range of the treating amount for the ionic surfactant.

It is preferable to incorporate a suitable adsorption inhibitor into the dissolution liquid for dissolving the drug in order to ensure further inhibition of loss of the physiologically active peptide or protein due to adsorption. The adsorption inhibitor includes, for example, an albumin (e.g. a bovine serum albumin (BSA), a human serum albumin (HSA) and other serum albumins), gelatin and other water-soluble proteins; an alkylbenzenesulfonate (e.g. a sodium salt) and other anionic surfactants, a $C_{8-20}$ alkyltrimethylammonium chloride, the alkylbenzyldi-methylammonium halide shown by the above formula [e.g. a $C_{8-20}$ alkylbenzyldimethylammonium chloride (benzalkonium chloride, hereinafter sometimes referred to as BAC), a 4-$C_{1-10}$ alkylphenyloxyethoxyethylbenzyl-dimethylammonium chloride (e.g. benzethonium chloride)] and other cationic surfactants, Tween 80 and other nonionic surfactants and other surfactants, or alkali metal salts (e.g. sodium chloride). The adsorption inhibitor should be incorporated in an amount of 0.00001 to 1 w/w %, preferably about 0.0001 to 0.5 w/w % and more preferably about 0.001 to 0.1 w/w %. Further, incorporation of an absorption accelerator (e.g. monoterpene, aliphatic monoglyceride, Azone (manufactured by Nelson), limonen, oleic acid, lauric acid, octanol) for accelerating or promoting absorption of the drug into the liquid for dissolving the drug is also effective. Such absorption accelerator should be added in a proportion of about 0.1 to 80 w/w %, preferably bout 0.5 to 50 w/w % and more preferably about 1 to 30 w/w %.

Further, it is effective to incorporate a humectant into the drug dissolution liquid. Use of the dissolution liquid containing such humectant ensures inhibition of transpiration of the drug dissolution liquid, provides long-term current applicability (electric conductivity) and hence ensures transdermal absorption (endermic delivery) of the drug with high bioavailability and excellent reproducibility.

The humectant is not particularly limited as far as being a substance which inhibits transpiration or evaporation of moisture from the drug dissolution liquid, and provides retention or reservation of moisture (water) in the skin surface, in the surface of the interface to be made contact with the skin and in the drug holder, and does not adversely affect the skin. The humectant includes, for instance, (1) polyhydric alcohols, (2) sugar alcohols, (3) amino acids and (4) acidic mucopolysaccharides. These humectants may be used singly or in combination.

The polyhydric alcohol (1) includes, for example, glycerin, ethylene glycol, propylene glycol, 1,3-bu-tylene glycol, pentaerythritol, polyethylene glycol, adducts in which ethylene oxide is added to these polyhydric alcohols (e.g. dioxyethylene glycol, trioxyethylene glycol, polyoxyethylene glycol, an ethylene oxide-propylene oxide copolymer, a glycerin-ethylene oxide adduct, a pentaerythritol-ethylene oxide adduct, etc.). Such polyhydric alcohols can be employed independently or in combination. Preferred examples of the polyhydric alcohol include polyhydric alcohols each having 2 to 4 hydroxyl group per molecule, in particular glycerin.

As the sugar alcohol (2), there may mentioned for example xylitol and other pentitols, sorbitol, mannitol, galactitol and other hexitols. These sugar alcohols may also be used singly or in combination.

Examples of the amino acid (3) include (i) an amino acid constituting a protein, (ii) a naturally-occurring amino acid derived or obtained as a metabolite of a microorganism, or an animal or plant component, and (iii) an amino acid obtained by organic synthesis.

(i) The amino acid constituting a protein includes glycine, alanine, valine, leucine, isoleucine and other aliphatic monoaminomonocarboxylic acids: serine, threonine and other aliphatic hydroxyamino acids, aspartic acid, glutamic acid and other acidic amino acids: asparagine, glutamine and other acidic amino acid amides; phenylalanine, tyrosine, tryptophane and other aromatic amino acids; proline, hydroxyproline and other amino acids each having pyrrolidine ring; pyroglutamic acid (pyrrolidone-carboxylic acid) and other amino acids having pyrrolidone ring; arginine, lysine, histidine and other basic amino acids: methionine, cystine, cysteine and other sulfur-containing amino acids, for instance. Such amino acids may be employed independently or in combination.

(ii) As the naturally-occurring amino acid derived or obtained as a metabolite of a microorganism or an animal or plant component, there may be mentioned, for example, L-α-aminobutyric acid, γ-aminobutyric acid, β-aminoisobutyric acid, β-alanine, homoserine, α-methyl-D-serine, O-carbamyl-D-serine, δ-hydroxy-γ-oxo-norvaline and other aliphatic monoaminomonocarboxylic acids: L-α-aminoadipic acid, L-β-aminoadipic acid, L-theanine, L-γ-methyleneglutamic acid, L-γ-methylglutamic acid and other monoaminodicarboxylic acids; L-ornithine, β-ly-sine, α,β-diaminopropionic acid, L-α,γ-diaminobutyric acid and other diaminomonocarboxylic acids; diamino-pimeric acid and other diaminodicarboxylic acids; cysteic acid and other sulfonic acid-containing monoamino-monocarboxylic acids; taurine and other sulfonic acid-containing amino acids; kynurenine, 3,4-dioxyphenyl-L-alanine and other aromatic amino acids; 2,3-dicarboxy-aziridine, [S]-2-amino-3-(isoxazolin-5-on-4-yl)propionic acid, anticapsin and other heterocyclic amino acids; L-4-oxalysine, L-4-oxolysine, [3R,5R]-3,6-diamino-5-hydroxyhexanoic acid and other basic amino acids; lanthionine, S-methyl-L-cysteine and other sulfur-containing amino acids: pipecolic acid, azetidine-2-carboxylic acid, [1R,2S]-2-aminocyclopentane-1-carboxylic acid and other cyclic amino acids: citrulline, alanosine, azaserine and other amino acids substituted with a specific functional group so forth.

Examples of (iii) the amino acid obtained by organic synthesis include trimethylglycine, 6-amino-hexanoic acid, 8-aminooctanoic acid, 12-aminododecanoic acid and other aliphatic aminocarboxylic acids; 4-amino-benzoic acid, 4-(aminomethyl)benzoic acid, 4-(N-(carboxymethyl) aminomethyl)benzoic acid and other aromatic aminocarboxylic acids.

The amino acid may be used in the form of a salt. The salt of the amino acid includes, for example, a salt with a base [e.g. ammonia, alkali metals (e.g. sodium, potassium) and other inorganic basis, and trimethylamine, triethylamine and other organic basis], and a salt with an acid [hydrochloric acid, sulfuric acid, nitric acid, phosphoric acid and other inorganic acids, and acetic acid, propionic acid, p-toluenesulfonic acid and other organic acids].

Preferable amino acid includes amino acids each having a nitrogen-containing heterocycle (e.g. proline, hydroxyproline and other amino acids having pyrrolidine ring, pyrrolidonecarboxylic acid, histidine, tryptophane and other amino acids constituting a protein) or salts thereof. Among them, amino acids each having nonaromatic nitrogen-containing 5-membered heterocycle (e.g. amino acids having pyrrolidine ring such as proline, hydroxyproline and pyrrolidonecarboxylic acid) or salts thereof can advantageously be employed.

(4) The acidic mucopolysaccharide includes, for instance, hyaluronic acid, chondroitin sulfate, and their salts [e.g. salts with alkali metals (e.g. sodium, potassium)].

Among these humectants, polyhydric alcohols (in particular glycerin) and amino acids or salts thereof (in especial, proline and other amino acids each having a nitrogen-containing heterocycle) may preferably be used. The use of the amino acid (in particular, proline and other amino acids each having a nitrogen-containing heterocycle) or its salt ensures remarkable mitigation of skin irritation accompanied with an electric current application, and provides an increased quantity of applied electricity in an application of an electric current succeeding to the first application of current in a case that transdermal absorption is conducted in plural times at periodic intervals, and hence ensures an improved transdermal absorptivity.

The content of the humectant in the drug dissolution liquid comprising an aqueous solution may be selected from a suitable range, according to the species of the humectant, which ensures suppression of transpiration of moisture from the drug dissolution liquid and reserves the moisture on the surface of the skin and in the drug-supporter (drug-holder). The content of the humectant is, for example, about 1 to 90% by weight, preferably about 1 to 80% by weight (e.g. about 5 to 80% by weight). and more preferably about 1 to 50% by weight based on the amount of the dissolution liquid for dissolving the drug. Among them, the amino acid and its salt ensures a high retention of moisture even used in a small amount. In more concretely, when the humectant is a polyhydric alcohol such as glycerin, the content of the humectant in the drug dissolution liquid is, for instance, about 5 to 50% by weight (e.g. about 10 to 50% by weight), and preferably about 20 to 40% by weight. When the humectant is the amino acid or its salt, the proportion of the humectant in the drug dissolution liquid is about 1 to 30% by weight, preferably about 5 to 25% by weight, and more preferably about 10 to 20% by weight, generally speaking.

The humectant may be held or supported by the hydrophilic membrane if necessary together with the drug and/or the ionic surfactant.

When the drug is a physiologically active peptide or protein, a dissacharide (e.g. trehalose, maltose, mannitol and inositol) may be added to the aqueous solution containing the drug for the purpose of improvement of stability of the drug in dry conditions. The proportion of the dissacharide is, for example, about 0.1 to 10 mg/ml, and preferably about 1 to 5 mg/ml (e.g. about 1 to 4 mg/ml).

Long-term preservation of the drug held or supported by the membrane (drug holder or drug retainer) with maintaining activities of the drug can be effected by storing the drug in dry condition. More concretely, preservation of the drug in dry condition may be conducted by, for instance, a process which comprises efficiently drying the drug holder holding the drug, and packaging the drug holder with a film having a small water permeability (e.g. an aluminum film) by vacuum sealing method. Further, in order to retain the dry condition with certainty, the drug holder supporting the drug may be vacuum-sealed and packaged together with a desiccating agent or dryer (e.g. a zeolite-based desiccator such as "SELAM" manufactured by Tokai Chemical Industries, Ltd., a silica gel-based desiccator, etc.). When the drug is to be oxidatively decomposed, an oxygen absorbent (e.g. "AGELESS" manufactured by Mitsubishi Gas Chemical Co., Ltd.) may be incorporated into the package in addition to the desiccating agent.

Figure 2:
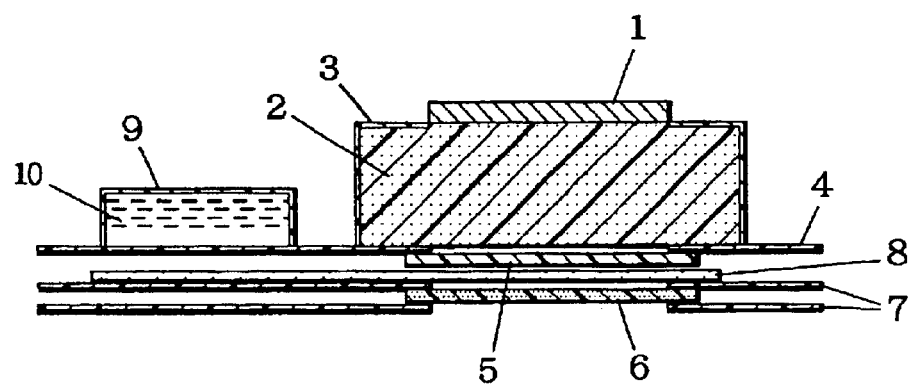
FIG. 2 is a cross sectional view illustrating another embodiment of an applicator.

The interface composed of the membrane is useful for transdermal delivery (endermic administration) of the drug by means of iontophoresis using a variety of applicators which are applicable to a skin. FIG. 1 and FIG. 2 respectively show a cross sectional view illustrating an embodiment of the applicator provided with the interface.

The applicator shown in FIG. 1 is provided with a support (base member) 4 having flexibility and being formed with an opening 20, and a container (reservoir) 3 disposed in a part of the support 4 corresponding to the opening 20. The container 3 is provided with an electrode 1 such as a silver electrode, and accommodates electric conductor 2 such as an electric conductive non-woven fabric or sponge containing water or an electric conductive gel such as an water-containing gel, polyvinyl alcohol (PVA) comprising NaCl. In the part of the support 4 corresponding to the opening 20 are disposed an ion exchange membrane 5, the inner surface of which faces to the electric conductor 2 of the container 3, and an interface (hydrophilic membrane) 6 as laminated by means of an adhesive tape 7. The adhesive tape 7 is utilized for attaching or applying the applicator to the skin. The electric conductor 2 of the container 3 is conductible to the electrode 1 and capable of making contact with the ion exchange membrane 5 through the opening 20. Further, an injection port 21, to which a liquid is injectable, is formed between the ion exchange membrane 5 and interface 6.

When such an applicator is used, a nozzle tip of an injection tip 8 may be inserted to the injection port 21 between the ion exchange membrane 5 and the interface 6 to inject a solution containing the drug, or when the interface holds or supports the drug, the drug dissolution liquid such as a distilled water for injection application to the interface 6. The amount of the liquid to be injected may be selected from a range according to the size of the applicator, the surface area of the interface, and the holding amount of the drug, and is usually about 30 to 500 μl and preferably about 50 to 200 μl.

Incidentally, a second container (reservoir) 9 as a reservoir for reservation of a liquid for drug dissolution, such as a distilled water for injection, may be disposed in the opening distant from the container 3 in the support of the applicator in FIG. 2. An interface (hydrophilic membrane) 6 may be disposed on the outer surface of the ion exchange membrane 5 through a non-woven fabric 8 disposed in the area from the first container 3 toward the second container 9. When such an applicator is used, the second container 9 may be pierced by, for example, inserting a needle through the second container 9 and the support 4 to form a pore in the support connecting to the inside of the second container 9, so that the liquid 10 for dissolution of the drug or drug-containing solution is permeated to the nonwoven fabric 8 for dissolution of the drug held by the interface 6, or supplying the drug-containing solution to the interface 6.

The first and second containers 3, 9 can be formed by, for instance, polyethylene or other synthetic resins. As the ion exchange membrane, use may be made of various membranes each having ion exchange capability, such as "AC220 Membrane" (trade name) manufactured by Asahi Chemical Industries, Japan. As the nonwoven fabric, a variety of nonwoven fabrics, through which a liquid is permeable, such as "Benberg Half" (trade name) manufactured by Asahi Chemical Industries, Ltd. Japan, can be used. As the adhesive tape, use may be made of a variety of adhesive tapes each having adhesive properties with respect to a skin, such as "Blenderm" (trade name) manufactured by 3M Pharmaceuticals, M.N. (Minnesota).

Figure 3:
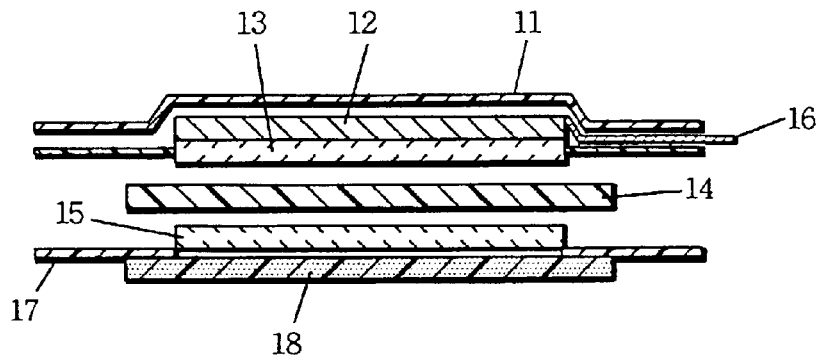
FIG. 3 is a cross sectional view showing another embodiment of an applicator.

In the applicator illustrated in FIG. 3, the basic structure of the applicator may comprise a container 11 (e.g. made from polyester) having a depression (hollow) to accommodate an electrode and an electrode 12 (e.g. round shaped foil-type electrode) disposed in the depression of the container 11, and to the side of the electrode are disposed, in turn, a nonwoven fabric 13 (e.g. WP-2085, Japan Vilene Co., Ltd.), an ion exchange membrane 14 (e.g. AC201 Membrane, Asahi Chemical Industries, Ltd., or an ion exchange filter paper, Toyo Roshi Co., Ltd.) and a nonwoven fabric 15 (e.g. LMW-9007 manufactured by Japan Vilene Co., Ltd.). Further, a connecting terminal 16 is installed on the electrode part in such a manner as being connectable or conductible to an electric power supply. A hydrophilic membrane 18 holding or supporting a drug, which is applied to an adhesive tape 17 (e.g. Blenderm, manufactured by 3M Pharmaceuticals, M.N. (Minnesota)) is applied to the applicator in such a manner that the drug-holding membrane makes contact with a skin. Incidentally, a liquid for electric conductive layer and the drug dissolution liquid may practically be incorporated or impregnated into the nonwoven fabrics 13 and 15.

The transdermal delivery (endermic administration) of the drug by means of iontophoresis can be effected by applying an electric voltage to the electrode of the applicator and a reference electrode to pass an electricity. As the electric current voltage, an alternating current voltage may be employed but use is practically made of a direct current voltage. As such direct current voltage, not only a continuous direct current voltage but also a depolarizing direct current pulse voltage can be utilized. Preferably, use may be made of an electric power supply which can apply a depolarizing pulse direct current voltage, in particular, a square pulse direct current voltage. The frequency of the pulse direct current voltage may be selected within a range of, for example, about 0.1 to 200 kHz, preferably about 1 to 100 kHz and more preferably about 5 to 80 kHz. The ON/OFF ratio of the pulse direct current voltage is, for instance, about 1/100 to 20/1, preferably about 1/50 to 15/1 and more preferably about 1/30 to 10/1. The applied voltage may be selected from a range not injuring a skin of a living body and not adversely affecting the transdermal absorption ratio, and is, for instance, about 1 to 20 V, and preferably about 3 to 15 V. The current application time per day is, for example in continuous application of the current, not longer than 24 hours, preferably not longer than 12 hours and particularly not longer than 6 hours. In an intermittent current application, the total of the current application time is preferably not longer than 24 hours, more preferably about not longer than 12 hours and particularly not longer than 6 hours.

The interface of the present invention, in which the hydrophilic membrane having a low adsorptivity for a protein is applied to a surface to be made contact with a skin, ensures efficient transdermal drug delivery by means of iontophoresis with a high bioavailability and sufficient reproducibility while controlling the dose with excellent accuracy or precision. Further, the use of the hydrophilic membrane provides improved releasability of the drug, and ensures high permeability of the drug and hence effective administration of the drug. Furthermore, even if the drug is the physiologically active peptide or protein, it ensures high releasability and high permeability of the drug, and hence provides enhanced bioavailability of the physiologically active peptide or protein.

The following examples are intended to illustrate the present invention in more detail, but should by no means limit the scope of the invention.

EXAMPLES

In the following Example 1 and Comparative Examples 1 and 2, an abdominal skin of a male SD rat (7-week aged) was clipped with a hair clipper and treated with a shaver under pentobarbital-anesthetization, and was rubbed slightly with an absorbent cotton containing a 70% aqueous solution of ethanol for defatting and disinfection. The applicator shown in FIG. 1 provided with the interface of the invention is applied to the abdominal skin of the rat, and a silver chloride electrode (2.5 cm$^2$) as a reference electrode (cathode) composed of 10% PVA gel (NaCl content 0.9%, thickness 2 mm) was fixed to the skin beside the applicator (anode). The iontophoresis was conducted by standing still the applicator for 1 hour after application to the skin without electric current application, repeating three times a cycle composed of applying a depolarizing pulse direct current (40 kHz; duty 30%; electric voltage 12 V) for 15 minutes and ceasing or interrupting the current application for 5 minutes. The peptide concentration in serum was determined by the radioimmunoassay method.

Example 1

A peptide fragment (hPTH (1→34)) of the N-terminal of a human parathyroid hormone (PTH) (40 µg per membrane) was held, in dry conditions, to a hydrophilized poly (vinylidene fluoride) membrane (Millipore Co., Ltd., "Hydrophilic Durapore", thickness 125 µm, mean pore size 5 µm, porosity 70%, membrane area 3.5 cm, adsorptivity for a protein 3 µg/cm$^2$) to give an interface. This interface was applied and fixed to the abdominal skin of the rat by means of an adhesive tape as a surface to be made contact with the skin. Thereafter, 100 µl of a distilled water containing 0.003% of benzalkonium chloride (BAC) was supplied from an injection port through the injection tip for dissolution of the peptide, and hence the peptide was transdermally delivered by means of iontophoresis. The peptide concentration in serum was determined. This procedure was repeated three times for different rats.

Example 2

The hydrophilized poly(vinylidene fluoride) membrane used in Example 1 was applied and fixed, as the surface to be contacted with the skin, to the abdominal skin of the rat with the use of an adhesive tape. A distilled water (120 µl) containing 40 µg of hPTH (1→34) and 0.0025% of BAC was supplied or fed from the injection port through the injection tip for transdermal peptide administration by iontophoresis, and the peptide concentration in serum was determined. This procedure was repeated 4 times for different rats.

Comparative Example 1

By using an applicator having no hydrophilic membrane, 120 µl of a distilled water containing 40 µg of hPTH (1→34) and 0.0025% of BAC was supplied from the injection port, via the injection tip, to the applicator, and the peptide was transdermally administered by iontophoresis. The peptide concentration in serum was determined. Such procedure was repeated 4 times with respect to different rats.

Comparative Example 2

To a surface-modified nylon membrane (Nippon Pall Co., Ltd., Biodyne Plus, thickness 150 µm, membrane area 3.5 cm$^2$, adsorptivity for a protein 13 µg/cm$^2$) treated with 0.01% BAC was held, in dry conditions, 40 µg per membrane of hPTH (1→34) to prepare an interface. The obtained interface was applied and fixed, as the side to contact a skin, to the abdominal skin of the rat using the adhesive tape. Through the injection tip was supplied 120 µl of a distilled water from the injection port to dissolve the peptide and hence the peptide was transdermally administered by means of iontophoresis, and the concentration of the peptide in serum was determined. This procedure was repeated 5 times for different rats.

Figure 4:
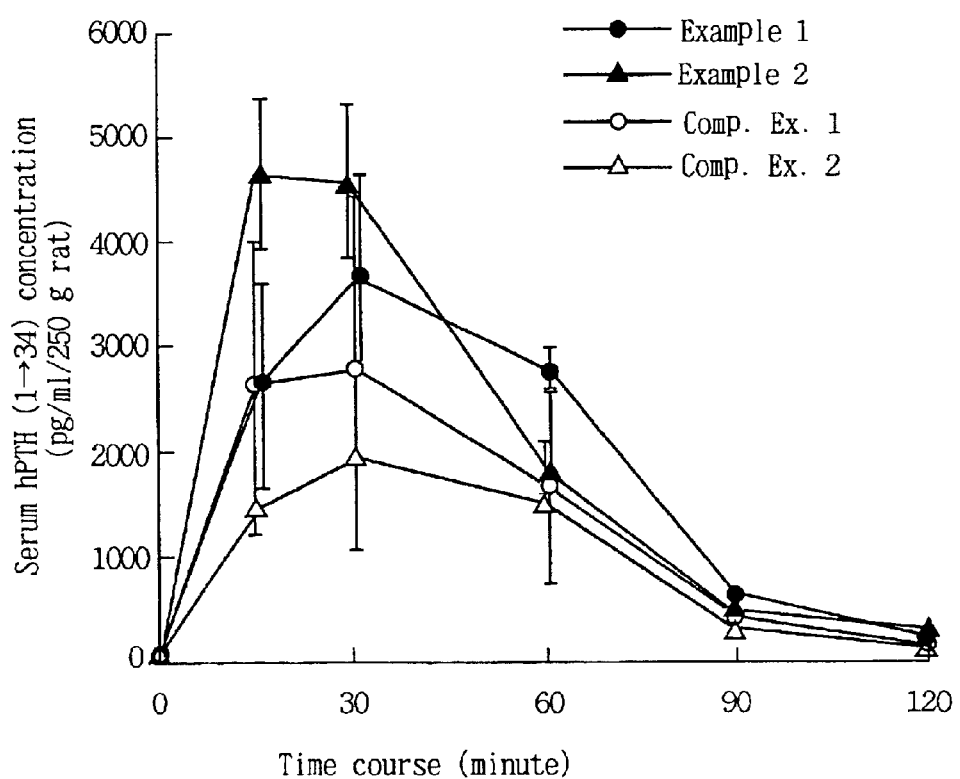
FIG. 4 is a graph showing the results in Examples 1 and 2, and Comparative Examples 1 and 2.

The results obtained in the examples and comparative examples are set forth in FIG. 4.

As apparent from FIG. 4, higher peptide concentration in serum was obtained with excellent reproducibility in Example 1 and Example 2 when compared with Comparative Example 1 and Comparative Example 2. The drug bioavailability was evaluated as the ratio of the area under the serum hPTH concentration-time curve (AUC value) of the tested group relative to the AUC value obtained by Intravenous administration on same dose basis [actual intravenous dose, 2 μg/kg of hPTH (1→34)]. The drug bioavailabilities of Example 1 and Example 2 were 12.8% and 14.0% respectively, while those of Comparative Example 1 and Comparative Example 2 were 9.2% and 6.7%, respectively. Thus, according to the examples, extremely high bioavailabilities were obtained with excellent reproducibility.

Examples 3–4 and Comparative Examples 3–4

In order to examine the drug adsorptivity, to the membranes as shown below were held 40 μg, per membrane, of hPTH (1→34) and a tracer scale of $^{125}$I-labelled hPTH (1→34) in dry conditions. The membranes were dipped into 300 μl of a distilled water at room temperature, and were pulled up after a predetermined time elapsed. The radioactivity of the membrane was determined to calculate the releasing amount of hPTH (1→34) from the membrane. This procedure was repeated 3 times respectively for each example and comparative example.

Example 3: Hydrophilized poly(vinylidene fluoride) membrane used in Example 1

Example 4: Hydrophilized poly(vinylidene fluoride) membrane treated with 0.01% of BAC Comparative Example 3: Surface-modified nylon membrane used in Comparative Example 2

Comparative Example 4: Surface-treated nylon membrane treated with 0.01% of BAC

Figure 5:
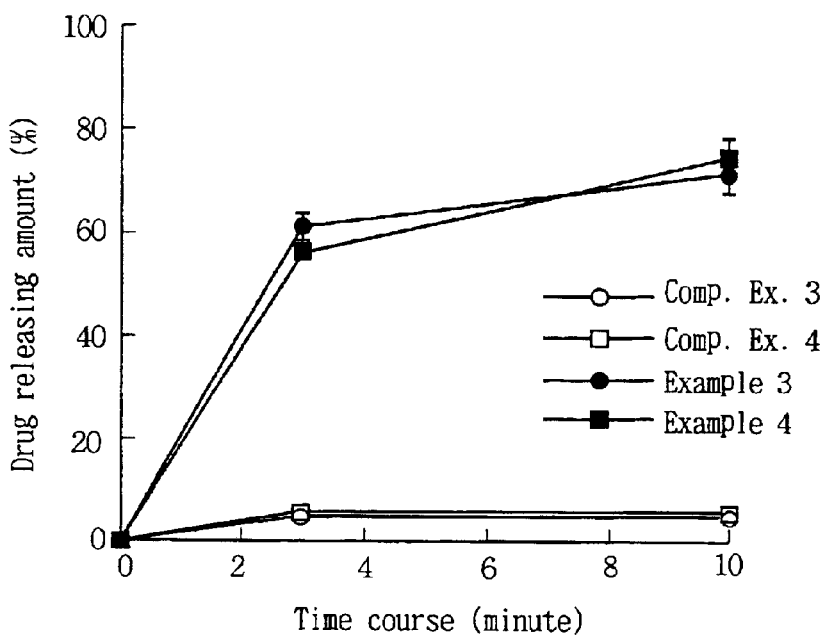
FIG. 5 is a graph illustrating the results in Examples 3 and 4, and Comparative Examples 3 and 4.

The results are illustrated in FIG. 5. As shown in FIG. 5, the hydrophilized poly(vinylidene fluoride) membrane without further treatment with surface active agents has low adsorptivity for the drug, and hence show extremely rapid release of the peptide.

Examples 5–6 and Comparative Examples 5–6

In order to examine the drug releasabilities, to the hydrophilized poly(vinylidene fluoride) membrane used in Example 1 (Example 5), a hydrophilized poly-(vinylidene fluoride) membrane treated with 0.01% of BAC (Example 6), the surface-modified nylon membrane without treatment with BAC used in Comparative Example 2 (Comparative Example 5) and a surface-modified nylon membrane treated with 0.01% of BAC (Comparative Example 6) were held, respectively per membrane, 40 μg of hPTH (1→34) and a tracer amount of a $^{125}$I-labelled hPTH (1→34). These membranes were dipped into 10 ml of a distilled water or 10 ml of a distilled water containing 0.01% of BAC, and stood still at 4° C. for 3 days. The releasing amount of the hPTH (1→34) from each membrane was calculated by determining radioactivity. The procedure was repeated 3 times with respect to each examples and comparative examples.

Figure 6:
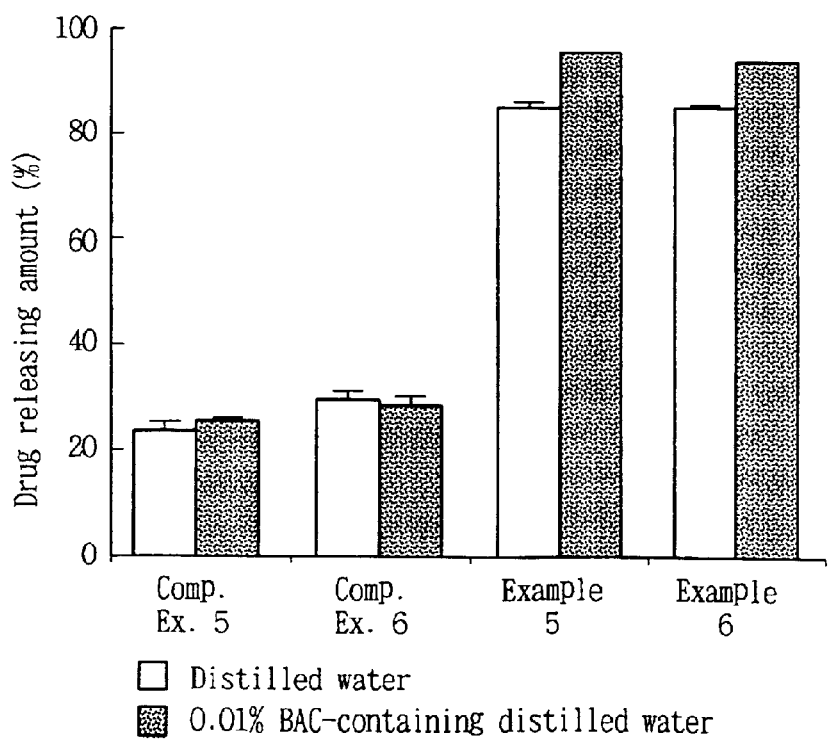
FIG. 6 is a graph showing the results in Examples 5 and 6, and Comparative Examples 5 and 6.

The results are shown in FIG. 6. As apparent from FIG. 6, the peptide was released or eluted from the membranes in a proportion of not greater than 30% according to Comparative Examples 5 and 6 respectively. In contrast, according to Examples 5 and 6, the peptide was released or eluted from the membranes in a proportion of not less than 80%, hence the membranes of Example 5 and Example 6 show low adsorptivity for the drug and remarkably rapid release of the peptide.

Example 7

Figure 7:
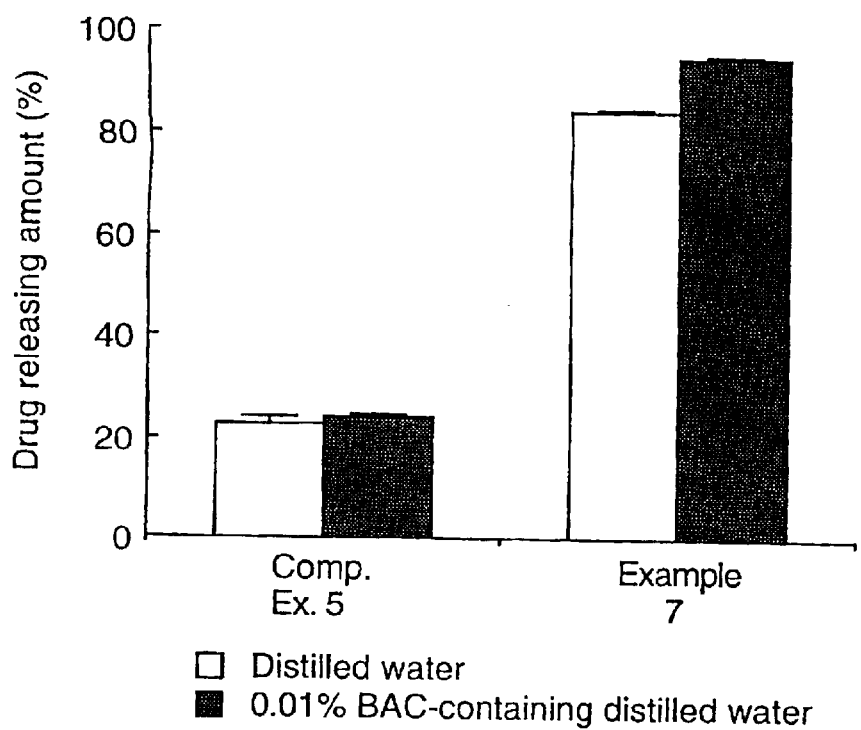
FIG. 7 is a graph illustrating the results in Example 7 and Comparative Example 5

To a Coated Type Membrane (polyester non-woven treated with cellulose acetate and wetting agents. Toyo Roshi Co., Ltd.) were held, respectively per membrane, 40 μg of hPTH (1→34) and a tracer amount of a $^{125}$I-labelled hPTH (1→34). With this membrane, a similar drug release test to that shown in FIG. 6 was conducted. The results are shown in FIG. 7.

The peptide was released or eluted from the membrane in a proportion of not less than 80%, hence the membrane of Example 7 shows low adsorptivity for the drug and remarkably rapid release of the peptide.

In the following Examples 8 to 10, an abdominal skin of a male SD rat (7-week aged) was clipped with a hair clipper and treated with a shaver under ether-anesthesia, and the skin was rubbed slightly with an absorbent cotton containing a 70% aqueous solution of ethanol for defatting and disinfection. To the side abdominal skin (skin in the lateral region) of the rat was applied the applicator shown in FIG. 3 provided with the interface of the present invention, and was applied a silver chloride electrode (2.5 cm $^2$), as a reference electrode (cathode), fixed on a 12% PVA gel (NaCl content 0.9%, thickness 2 mm). After application of the applicator and the reference electrode, the rat was fixed in a Ballmann cage.

In the applicator shown in FIG. 3, 100 to 200 μl of a citric acid buffer (33 mM, pH 5) containing 10% of L-proline was impregnated to the nonwoven fabrics 13 and 15. Incidentally, the applicator comprised the container 11 (made from a polyester, inner diameter 21 mm), the silver electrode 12 (round, foil-shaped silver electrode, diameter 18 mm, thickness 0.04 mm), the nonwoven fabric 13 (WP-2085, Japan Vilene Co., Ltd.; diameter 18 mm, thickness 0.63 mm), the ion exchange membrane 14 (AC201 Membrane, manufactured by Asahi Chemical Industries, Ltd.: diameter 21 mm, thickness 0.23 mm), the nonwoven fabric 15 (LMW-9007 manufactured by Japan Vilene Co., Ltd.: diameter 18 mm, thickness 0.23 mm), connecting terminal 16, the adhesive tape 17 (Blenderm, 3M Pharmaceuticals) having a pore of 18 mm diameter and the hydrophilic membrane 18 (diameter 21 mm).

In the iontophoresis, the electric current application was conducted by using a depolarizing pulse direct current (frequency 30 kHz, ON/OFF ratio 3/7, electric voltage 10 V) by means of a short-circuit switch, repeating, three times, a pattern which comprises applying electric current for 45 minutes (applying electric current for 15 minutes, interrupting the current application for 5 minutes, and repeating this process three times in total), and interrupting the current application for 60 minutes. The peptide concentration in serum was then determined by the radioimmunoassay method. Such procedure was repeated 4 or 5 times for different rats.

Example 8

By employing an interface, as prepared by allowing the hydrophilized poly(vinylidene fluoride) membrane used in Example 1 to hold 200 μg per membrane of hPTH (1→34) in dry conditions, transdermal administration of the peptide was conducted.

Example 9

The peptide was administered transdermally by using an interface as prepared by allowing a cellulose acetate membrane (Toyo Roshi Co., Ltd., Cellulose Acetate Type Membrane: thickness 125 μm, mean pore size 5 μm, porosity 72%, membrane area 3.5 cm²) to hold 200 μg per membrane of hPTH (1→34) in dry conditions.

Example 10

By using an interface as produced by allowing a hydrophilized polytetrafluoroethylene membrane (Millipore Co., Ltd., Omnipore; thickness 80 μm, mean pore size 10 μm, porosity 80%, membrane area 3.5 cm²) to hold 200 μg per membrane, of hPTH (1→34) in dry conditions.

Figure 8:
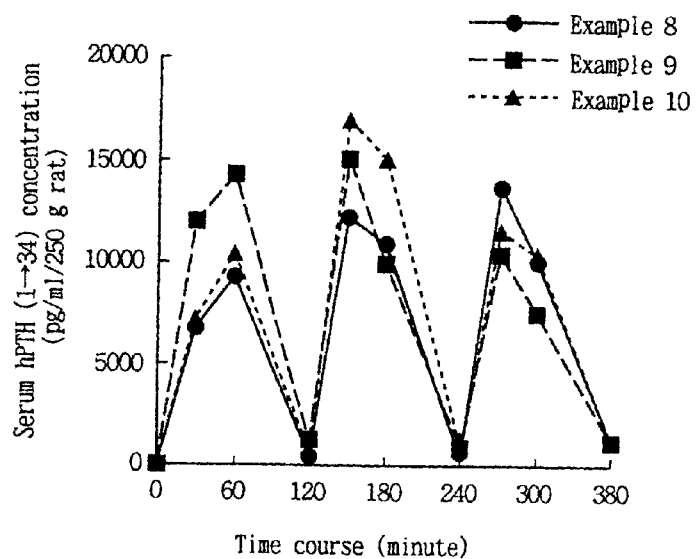
FIG. 8 is a graph illustrating the results in Examples 8 to 10.

The mean values of the results each obtained in Examples 8 to 10 are illustrated in FIG. 8. As shown in FIG. 8, high serum concentration of the peptide was obtained according to each examples. The drug bioavailabities were evaluated from the ratio of the area under the serum hPTH concentration-time curve (AUC value) of the tested group relative to the AUC value obtained by intravenous administration on same dose basis [actual intravenous dose, 2 μg/kg of hPTH (1→34)]. The drug bioavailabilities of example 8, example 9 and example 10 were 29%, 32% and 33%, respectively, and remarkably high bioavailabities were obtained with excellent reproducibilities according to the examples.

What is claimed is:

1. An interface for iontophoresis which comprises a membrane having a low adsorptivity for a protein, wherein the membrane is (1) a hydrophilized fluororesin membrane of a homo- or co-polymer composed of a fluorine-containing monomer having a hydrophilic group as a constitutive unit, (2) a hydrophilized polysulfone membrane incorporating a wetting agent or (3) a hydrophilized cellulose derivative membrane.

2. The interface as claimed in claim 1, wherein the fluorine-containing monomer is a fluoroethylene having a hydrophilic group or a vinylidene fluoride having a hydrophilic group.

3. The interface as claimed in claim 1, wherein the hydrophilized fluororesin is at least one member selected from the group consisting of a polyfluoroethylene, a fluoroethylene-tetrafluoroethylene copolymer, a fluoroethylene-hexafluoropropylene copolymer, an ethylene-fluoroethylene copolymer, an ethylene-chlorotrifluoroethylene copolymer, a poly(vinylidene flouride, a fluoroethylene-vinylidene fluoride copolymer and an ethylene-vinylidene fluoride copolymer, and is introduced with a hydrophilic group.

4. The interface as claimed in claim 1, wherein the hydrophilic group is at least one member selected from the group consisting of a hydroxyl group, a carboxyl group, an amino group, a mono- or di-$C_{1-4}$ alkylamino group, an ether group, a hydroxy-$C_{1-4}$ alkyl group, a carboxy-$C_{1-4}$ alkyl group, an amino-$C_{1-4}$ alkyl group and a mono- or di-$C_{1-4}$ alkylamino-$C_{1-4}$ alkyl group.

5. The interface as claimed in claim 1, wherein the hydrophilic group is a hydroxy-$C_{2-3}$ alkyl group or a (poly) oxyalkylene group.

6. The interface as claimed in claim 1, wherein the membrane has an adsorptivity for a protein of 0 to 10 μg per 1 cm².

7. The interface as claimed in claim 1, wherein the membrane has a thickness of 1 to 300 μm.

8. The interface as claimed in claim 1, wherein the membrane is a porous membrane having pores with a mean pore size of 0.01 to 20 μm.

9. The interface as claimed in claim 1, wherein the membrane has a porosity of 60 to 90%.

10. The interface as claimed in claim 1, wherein the ionic surfactant is a cationic surfactant.

11. The interface as claimed in claim 1, wherein the ionic surfactant is a quaternary ammonium salt.

12. The interface as claimed in claim 1, wherein the ionic surfactant is an alkylbenzyldimethylammonium halide shown by the following formula

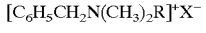

$$[C_6H_5CH_2N(CH_3)_2R]^+X^-$$

wherein R represents an alkyl group and X represents a halogen atom.

13. The interface as claimed in claim 1, wherein the membrane has a thickness of 10 to 200 μm and an area of 1 to 10 cm².

14. The interface as claimed in claim 1, wherein the hydrophilized fluororesin membrane is a poly(vinylidene flouride) and wherein the hydrophilic group is a hydroxy-$C_{2-3}$ alkyl group.

* * * * *